(12) United States Patent
Yu et al.

(10) Patent No.: US 11,471,561 B2
(45) Date of Patent: *Oct. 18, 2022

(54) INJECTABLE COMPOSITE MATERIAL FOR BONE REPAIR, AND PREPARATION METHOD THEREOF

(71) Applicant: Hangzhou Huamai Medical Devices Co., Ltd., Zhejiang (CN)

(72) Inventors: Chunhua Yu, Zhejiang (CN); Hua Liao, Hubei (CN); Xiaohua Yu, Zhejiang (CN); Tao Jiang, Zhejiang (CN)

(73) Assignee: Hangzhou Huamai Medical Devices Co., Ltd., Hangzhou (CN)

( * ) Notice: Subject to any disclaimer, the term of this patent is extended or adjusted under 35 U.S.C. 154(b) by 371 days.

This patent is subject to a terminal disclaimer.

(21) Appl. No.: 15/762,023

(22) PCT Filed: Nov. 21, 2016

(86) PCT No.: PCT/CN2016/106559
§ 371 (c)(1),
(2) Date: Mar. 21, 2018

(87) PCT Pub. No.: WO2017/097105
PCT Pub. Date: Jun. 15, 2017

(65) Prior Publication Data
US 2018/0264172 A1    Sep. 20, 2018

(30) Foreign Application Priority Data
Dec. 7, 2015  (CN) .......................... 201510891068.8

(51) Int. Cl.
| | | |
|---|---|---|
| *A61L 27/36* | (2006.01) | |
| *A61L 27/38* | (2006.01) | |
| *A61L 27/44* | (2006.01) | |
| *A61L 27/46* | (2006.01) | |
| *A61L 27/54* | (2006.01) | |

(52) U.S. Cl.
CPC ......... *A61L 27/3633* (2013.01); *A61L 27/365* (2013.01); *A61L 27/3687* (2013.01); *A61L 27/3691* (2013.01); *A61L 27/3834* (2013.01); *A61L 27/44* (2013.01); *A61L 27/446* (2013.01); *A61L 27/46* (2013.01); *A61L 27/54* (2013.01); *A61L 2300/412* (2013.01); *A61L 2300/64* (2013.01); *A61L 2400/06* (2013.01); *A61L 2430/02* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 7,189,263 B2 | 3/2007 | Erbe et al. | |
| 7,531,004 B2 | 5/2009 | Bagga et al. | |
| 7,534,451 B2 | 5/2009 | Erbe | |
| 8,287,915 B2 | 10/2012 | Clineff et al. | |
| 8,435,552 B2* | 5/2013 | O'Brien | A61L 27/56 424/423 |
| 8,597,675 B2 | 12/2013 | Murphy et al. | |
| 8,968,797 B2 | 3/2015 | Murphy et al. | |
| 9,381,275 B2 | 7/2016 | Murphy et al. | |
| 2002/0055143 A1* | 5/2002 | Bell | A61L 27/3633 435/69.1 |
| 2005/0013870 A1* | 1/2005 | Freyman | A61L 27/3633 424/520 |
| 2005/0013872 A1* | 1/2005 | Freyman | A61K 35/28 424/549 |
| 2005/0169893 A1 | 8/2005 | Koblish et al. | |
| 2005/0169956 A1 | 8/2005 | Erbe et al. | |

(Continued)

FOREIGN PATENT DOCUMENTS

| | | |
|---|---|---|
| CN | 101417145 A | 4/2009 |
| CN | 101816808 A | 9/2010 |

(Continued)

OTHER PUBLICATIONS

MedicineNet, https://www.medicinenet.com/script/main/art.asp?articlekey=7368 (Accessed May 19, 2020) (Year: 2020).*
Dennis et al., Langmuir, 33:206-218 (2017) (Year: 2017).*
Hench et al., J. Mater. Sci: Mater. Med., 17:967-9 78 (2006) (Year: 2006).*
Huang et al., Cerm. Internat., 41:8773-8778 (2015) (Year: 2015).*
Liu et al., J. Bionic Eng. Suppl., 001-008 (2008) (Year: 2008).*
Wolf et al., Biomater., 33:7028-7038 (2012) (Year: 2012).*
Baino et al., J. Funct. Biomater., 9(25):1-26 (2018) (Year: 2018).*
Gu Xian Yi Shin "Composite material for Bone Repair Based on Accellular Tissue Matrix and Its Preparation" Jun. 27, 2019. Dermis, Chapter 1 pp. 13-17.

(Continued)

*Primary Examiner* — Michelle F. Paguio Frising
(74) *Attorney, Agent, or Firm* — Blank Rome LLP (57) ABSTRACT

An injectable composite material for bone repair comprises a biological tissue material and bioceramics in order to serve as a three-dimensional scaffold for bone regeneration. The biological tissue material consists of microfibers having a naturally cross-linked structure without additional physical or chemical cross-linking, has superior biological compatibility, and can be slowly and completely degraded in vivo. The bioceramics in the composite material serves as a reinforcing phase. When combining the biological tissue material with the bioceramics, the composite material provides a template for bone tissue regeneration to effectively induce bone growth. The injectable composite material for bone repair can be used to fill bone defects, particularly critical-sized bone defects, and can be combined with a biological agent such as bone marrow to improve its biological activity. Therefore, the composite material can be widely used to repair bone defects caused by trauma, tumor resection, osteonecrosis, and infection.

8 Claims, 4 Drawing Sheets

(56) References Cited

U.S. PATENT DOCUMENTS

| | | |
|---|---|---|
| 2005/0208094 A1* | 9/2005 | Armitage ............... A61K 33/06 424/423 |
| 2005/0214340 A1 | 9/2005 | Erbe et al. |
| 2009/0157182 A1 | 6/2009 | Koblish et al. |
| 2009/0312524 A1* | 12/2009 | Lauritzen ............... A61K 38/17 530/356 |
| 2010/0129416 A1 | 5/2010 | Murphy et al. |
| 2012/0107383 A1* | 5/2012 | McKay ................. A61K 31/22 424/423 |
| 2012/0237568 A1 | 9/2012 | Murphy et al. |
| 2013/0177648 A1* | 7/2013 | O'Brien ................. A61L 27/46 424/484 |
| 2014/0255489 A1 | 9/2014 | Shi |
| 2015/0010510 A1* | 1/2015 | Badylak ............... C12N 5/0654 424/93.1 |
| 2015/0065947 A1 | 3/2015 | Wallace et al. |
| 2015/0133578 A1 | 5/2015 | Murphy et al. |
| 2015/0343117 A1 | 12/2015 | Ling et al. |
| 2016/0199537 A1* | 7/2016 | Koob ................... A61L 15/325 424/583 |
| 2016/0199540 A1* | 7/2016 | Liu .................... A61L 27/3687 424/574 |
| 2016/0279294 A1 | 9/2016 | Murphy et al. |
| 2017/0232144 A1* | 8/2017 | Kelly ................. A61L 27/3695 424/423 |

FOREIGN PATENT DOCUMENTS

| | | | |
|---|---|---|---|
| CN | 102874782 | A | 1/2013 |
| CN | 103432627 | A | 12/2013 |
| CN | 103566409 | A | 2/2014 |
| CN | 105311681 | A | 2/2016 |
| WO | WO-00/07639 | A1 | 2/2000 |
| WO | WO-2013/059089 | A1 | 4/2013 |
| WO | WO 2015/027727 | A1 | 3/2015 |
| WO | WO 2015/031809 | A1 | 3/2015 |
| WO | 2017097105 | A1 | 6/2017 |

OTHER PUBLICATIONS

State Intellectual Property Office of the P.R. China; PCT International Search Report, Issued in Connection to PCT/CN2016/106559; dated Mar. 7, 2017; 12 pages; China.

State Intellectual Property Office of the P.R. China; PCT Written Opinion of the International Searching Authority, Issued in Connection to PCT/CN2016/106559; dated Mar. 7, 2017; 5 pages; China.

結合組織の 定義と分類 Definition and classification of connective tissue, 2008, URL:www.kms.ac.jp/~anatomy2/Histology6.pdf, p. 1-32.

たらしい 皮膚科学 Hiroshi Shimizu, Textbook of modern dermatology, 2011, edition 2, p. 13-16.

International Search Report EP 16872297 dated Apr. 29, 2019.

Ehab Kheir et al. "Development and Characterization of an Acellular Porcine Cartilage Bone Matrix for Use in Tissue Engineering", Journal of Biomedical Materials Research Part A, vol. 99A, No. Nov. 19, 2011, pp. 283-294.

Crapo et al., "An Overview of Tissue and Whole Organ Decellularization Processes" Biomaterials, Elsevier Science Publishers BB., Barking, GB, vol. 32, No. 12, Jan. 19, 2011, pp. 3233-3243.

Benders et al. "Extracellular Matrix Scaffolds for Cartilage and Bone Regeneration" Trends in Biotechnology, Elsevier Publications, Cambridge, GB, V. 31, No. Jan. 5, 2013, pp. 169-176.

\* cited by examiner

INJECTABLE COMPOSITE MATERIAL FOR BONE REPAIR, AND PREPARATION METHOD THEREOF

CROSS-REFERENCE TO RELATED APPLICATION(S)

This application is a 35 U.S.C. § national application of International Patent Application No. PCT/CN2016/106559, filed Nov. 21, 2016, which designated the United States and was entitled "INJECTABLE COMPOSIT MATERIAL FOR BONE REPAIR, AND PREPARATION METHOD THEREOF," and claims priority to Chinese Patent Application No. 201510891068.8, filed on Dec. 7, 2015, the disclosures of which are incorporated by reference herein in their entirety.

TECHNICAL FIELD

The present invention belongs to the field of material science, and particularly to an injectable composite material for bone repair and the preparation method thereof. The composite material can be widely used in the field of orthopaedics and plastic surgery.

BACKGROUND

The repair and reconstruction of impaired bone tissues are important tasks that orthopaedic surgeons need to face all over the world. Bone grafting materials are needed in the repair of these bone tissues. Autologous bone tissues, i.e., healthy bone tissues harvested from the patient's own body, have been considered worldwide the golden standard for the repair of impaired bone tissues. The autologous bone has all the properties required for repairing bone tissues, such as excellent osteoinductivity, osteoconductivity, osteogenecity, and safety. However, there are clinically unavoidable disadvantages when using autologous bones. Since bone tissues need to be harvested from the donor site of the patient's body when using autologous bones, this additional surgery will increase the duration and cost of the surgery, and the recovery time for patients. At the same time, both the lesions in the donor site and the limitation of obtaining bone tissues from the donor site are the prominent problems currently.

The matrix of tissues and organs is a three-dimensional network composed of various complex structural and functional proteins, and contains many other active components. The main ingredients include collagen fibers, glycoproteins, mucins, etc. Other ingredients are saccharides such as glycosaminoglycans (hyaluronic acid, and chondroitin sulfate), some lipids, and growth factors. These ingredients can provide an excellent substrate for cell adhesion, and release a large amount of active peptides during its degradation process, which facilitate cell proliferation and differentiation.

Biological tissue matrix, as an ideal biological material, has almost all the characteristics required for tissue engineering and regenerative medicine. Therefore, it has been widely used in the repair and regeneration of various types of tissues and organs. At present, the biological matrices are extracted from various tissues such as small intestine, skin, liver, spleen, bladder, etc. Because of their different macro- and micro-structures, biomechanical properties, degradation rate in vivo and cell-matrix interactions, they have been used in the repair and regeneration of different tissues. Basically, all of the biological matrix products on the market exist in the form of membrane, which are roughly divided into two categories: dry and aqueous membranes. Their applications mainly focus on skin ulcers, peritoneal reconstruction, soft tissue regeneration, wound healing and meningeal trauma repair.

Because calcium phosphate-based bioceramics have inorganic ingredients similar to that of human bone tissues, and have excellent biocompatibility, biodegradability and osteoconductivity, they have been used in the preparation and modification of bone repair materials for a long time. Currently, the commonly used calcium phosphate bioceramics include hydroxyapatite, β-tricalcium phosphate, calcium hydrogen phosphate, and their composite ceramics. A large number of studies have shown that calcium phosphate bioceramics can absorb/enrich the proteins required for the formation of bones, facilitate the proliferation and differentiation of osteoblasts, and thereby induce the regeneration of new bones. Recent studies have shown that the calcium and phosphate ions released during the degradation of calcium phosphate bioceramics can positively affect osteoblasts and osteoclasts in the bone environment, and play an important role during the process of bone repair and regeneration. Therefore, the regulation of the degradation rate of bioceramics also becomes a new route to regulate their biological activity, which has great potential.

Currently, almost all of the commercially available bone repair materials involving biological agents use chemically purified type I collagen. The shortcomings of this type of collagen are that: the extraction process is complex, and the collagen is denatured during extraction, failing to exert its optimum biological performance; in addition, its composition are relatively simple, and cannot satisfy the needs of complex signaling pathway during bone repair process; furthermore, the chemical crosslinking agents with high toxicity are needed during the use of such collagen, which may easily induce immune and inflammatory response during implantation.

SUMMARY OF THE INVENTION

The objective of the present invention is to provide an injectable composite material for bone repair and the preparation method thereof. This new composite material is mainly comprised of two kinds of materials. Thus it not only possesses various advantages of natural biological matrix, such as strong bioactivity and cell behavior regulating capability etc., but also has excellent osteogenic ability to stimulate bone growth provided by inorganic materials such as bioceramics during bone repair process. The composite materials of the invention have an active bioscaffold with high osteoinductivity and osteogenicity. Therefore, they can rapidly induce the regeneration of new bones at the bone defects through multiple biological mechanisms. Meanwhile, the materials developed in this invention also avoid the major disadvantages, which affect the clinical efficacy in a large number of existing bone repair materials. Thus, the present invention provides an ideal technical solution for bone defect repair.

The objectives of the present invention are achieved by the following technical solutions.

An injectable composite material for bone repair, comprising the following raw materials in parts by weight: 1-7 parts of biological tissue matrix material, 1-9 parts of bioceramics and 2-8 parts of physiological saline or other isotonic aqueous solution.

Preferably, the biological tissue matrix material is an extracellular matrix maintaining its natural cross-linked structure, which is prepared from soft tissue of mammals, and is mainly comprised of collagen fibers.

Preferably, the soft tissue of mammals is a soft tissue of pig, a soft tissue of bovine or a soft tissue of human body. The soft tissue comprises skin, dermis, blood vessel, diaphragm, muscle tendon, ligament, large intestine, small intestine and nerve tissue.

Preferably, the biological tissue matrix material has a microfibrillar morphology. The microfibrillar biological tissue matrix material has a diameter of 1 to 1500 micrometers. The aspect ratio of the diameter to the length of the biological tissue matrix material is in the range of 0.05-0.95.

Preferably, the bioceramics can be replaced with bioglass, or minerals containing strontium, zinc, magnesium or silicon, or salts containing strontium, zinc, magnesium or silicon, as a material for reinforcing phase.

Preferably, the bioceramics are hydroxyapatite $[Ca_5(PO_4)_3OH]$, α-tricalcium phosphate, β-tricalcium phosphate $[α-Ca_3(PO_4)_2$ or $β-Ca_3(PO_4)_2]$, calcium hydrophosphate $[CaHPO_4]$, calcium hydrophosphate dihydrate $[CaHPO_4.2H_2O]$, calcium dihydrogenphosphate $[Ca(H_2PO_4)_2]$, tetracalcium phosphate $[Ca_4(PO_4)_2O]$, octacalcium phosphate $[Ca_8H_2(PO_4)_6.5H_2O]$, calcium sulfate $[CaSO_4]$ or calcium carbonate $[CaCO_3]$.

Preferably, the bioceramics are distributed in the form of particulates within the biological tissue matrix material. The bioceramic particles form a the three-dimensional network structure in the biological tissue matrix material.

Preferably, the bioceramic particles have a particle size of 1 to 500 micrometers.

A method for preparing the injectable composite material for bone repair comprises the following steps:

1) preparing a microfibrillar biological tissue matrix material, comprising the following steps:

1.1) collecting raw tissue material, cleaning off blood, cutting into long strips of 0.5-2 centimeters wide and 4-8 centimeters long, and preserving them at −20° C.;

1.2) disinfecting and sterilizing: sterilizing the tissue raw material by using ammonia aqueous solution with a mass concentration of 0.1%, soaking the raw tissue material in the solution and slowly shaking for 6-36 hours; washing sufficiently with sterile deionized water, and then rinsing with sterile physiological saline;

1.3) micronizing tissue: homogenizing the disinfected raw tissue strips by a grinder;

1.4) decellularizing raw tissue material with a decellularization solution, followed by removing the remaining deoxyribonucleic acid with deoxyribonuclease solution; and removing α-galactoside with a solution for α-galactoside removal; inactivating virus by a mixture solution of hydrogen peroxide, acetic acid and peroxyacetic acid;

1.5) washing the tissue matrix: using physiological saline with a mass concentration of 0.9% to wash the products in step 1.5) three or more times so as to remove the residues resulted from the treatment of step 1.4);

1.6) washing: washing the products in step 1.5) three or more times with sterile deionized water;

1.7) terminally sterilizing: after sterilizing with Co60 gamma rays, X-rays or electron beams, sealing and storing the resulting biological tissue matrix microfibers in a closed container, the biological tissue matrix material are preserved in a buffer with neutral pH, the buffer comprises physiological saline and phosphate buffer;

2) preparing bioceramic microparticles, comprising the following steps:

2.1) obtaining bioceramic microparticles with a particle size of 0.1-500 micrometers after the steps of mechanical pulverization, high-rate ball-milling, and sieving of the bioceramics according to specific application, and then disinfecting and sterilizing the bioceramic microparticles under high temperature and high pressure to inactivate virus;

2.2) mixing the bioceramic microparticles with sterile physiological saline in a ratio of 1:1 to 1:5, sufficiently stirring and vibrating to obtain a homogeneous suspension;

3) suspending the biological tissue matrix microfibers obtained in step 1.7) into physiological saline of a weight 1-5 times of that of the microfibers, and shaking sufficiently to obtain a homogeneous suspension of biological tissue matrix microfiber;

4) mixing the bioceramic particles with the biological tissue matrix microfibers in a ratio of raw materials according to the present invention;

5) placing the mixture on a vortex mixer and mixing sufficiently for one hour until the bioceramic particles are completely adsorbed onto the biological tissue matrix microfibers;

6) removing excess water by centrifugation at 200 to 10000 rpm, and allowing the mixture to be deposited on the bottom in solid state;

7) adding physiological saline of a weight 1-5 times of that of the mixture, placing them on the vortex mixer to form a homogeneous fluid mixture, wherein the moisture content in mass percent is 20-80%;

8) terminally sterilizing: sealing and storing the resulting fluid mixture in a closed container, and sterilizing with gamma rays, X-rays or electron beams.

Preferably, raw tissue material selected in step 1.1) is derived from the soft tissue of mammals, including skin, small intestine, large intestine, septum, bladder, stomach and muscle tendon.

Preferably, the decellularization solution in step 1.4) contains 1 to 10% of sodium deoxycholate, 2 to 15 mM of ethylenediaminetetraacetic acid, and 10 to 50 mM of 4-hydroxyethyl piperazine ethanesulfonic acid per liter. The pH of the decellularization solution is 6.8 to 7.2. The deoxyribonuclease solution contains 0.5 to 5 mg of deoxyribonuclease, 10 to 50 mM of 4-hydroxyethyl piperazine ethanesulfonic acid, 1 to 20 mM of calcium chloride, and 1 to 20 mM of magnesium chloride per liter. The solution for α-galactoside removal contains 0.2 to 10 mg of α-galactosidase, and 2 to 40 mM of 4-hydroxyethyl piperazine ethanesulfonic acid per liter. The pH of the solution for α-galactoside removal is 5.0 to 7.5. The solution used for inactivating virus is a mixture solution of 0.10% of hydrogen peroxide, 0.50% of acetic acid, and 0.50% of peroxyacetic acid.

Further, the solution for dispersing the bioceramic particles and the biological tissue matrix material, i.e., the physiological saline from step 7), is replaced by blood, bone marrow, or high concentration of platelet plasma.

Further, a method is provided for delivering stem cells to a bone defect, wherein cell suspensions are formed with bone marrow mesenchymal stem cells, adipose-derived stem cells or stem cells extracted from blood, and then mixed with the composite material for bone repair obtained according to the present invention, using as means for delivering stem cells to the bone defect.

The advantageous effects of the present invention are as follows: the present invention relates to an injectable biological composite material based on biological tissue materials and bioceramics, and the preparation method thereof. The composite material effectively combines biological tissue material and bioceramic, and forms an injectable three-dimensional scaffolding biomaterial. The biological tissue matrix material according to the present invention is a microfiber having a naturally crosslinked structure, which does not need additional physical or chemical crosslinking, has excellent biocompatibility, and can be completely degraded slowly in vivo. The biological tissue materials and the bioceramics can be combined in a variety of manner. In the composite material of the present invention, the bioceramics as a reinforcing phase, after combining with the biological tissue material, can provide a good template for the regeneration of bone tissue in vivo and can effectively induce bone growth. The injectable material prepared by the present invention can be used to seamlessly fill bone defect of any size, and biological agents including bone marrow are added during the process to further enhance its biological activity. Therefore, the material can be widely used in the bone defects caused by trauma, tumor resection, osteonecrosis, and infection, etc.

DETAILS OF THE INVENTION

The present invention will be described in detail with reference to the examples, which are intended to illustrate the invention rather than limit the invention.

Example 1: The Preparation and Characterization of Biological Tissue Matrix/Calcium Hydrophosphate Composite Material 1) A microfibrillar biological tissue matrix material was weighted, which was obtained from decellularized and antigen-extracted porcine dermis and sterilized by Co60 gamma rays. The material was suspended in 0.9% of physiological saline in a concentration of 10 mg/mL.

Figure 1:
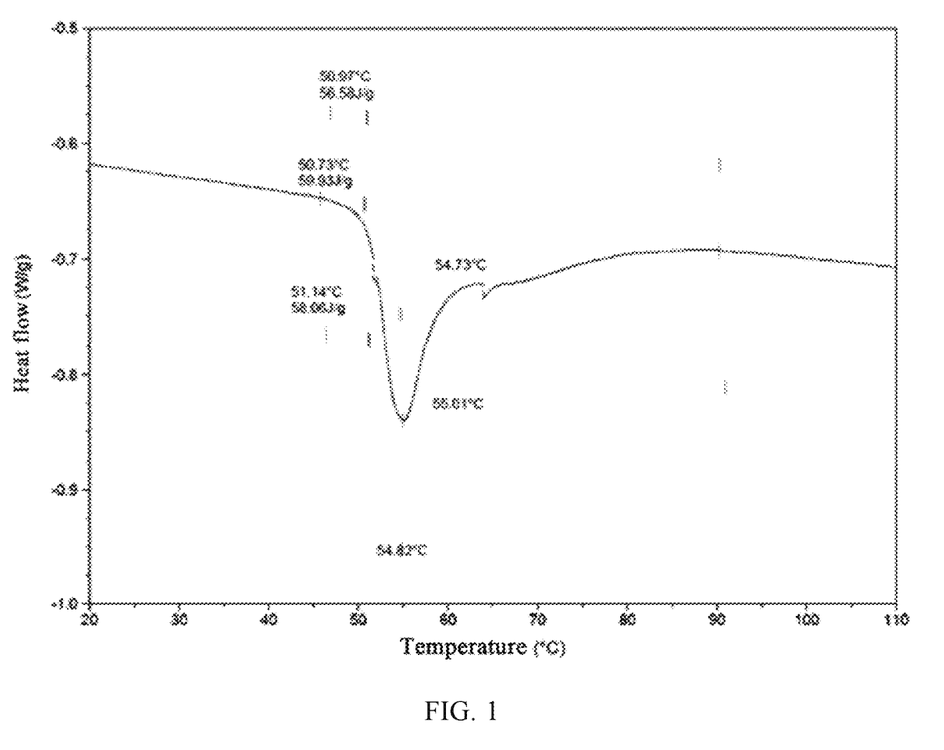
FIG. 1 is a diagram of differential scanning calorimetry of the biological tissue microfibers.

2) The material was washed 3 or more times with sterile deionized water. The parameters of the prepared decellularized matrix microfiber were shown in FIG. 1. It has an average aspect ratio of 0.05-0.95, and a particle size distribution of 40-1000 μm.

3) Calcium hydrophosphate microparticles were weighted and sterile deionized water was added to prepare a 10 mg/mL of homogeneous suspension.

4) The calcium hydrophosphate microparticles were rapidly passed through a filter membrane with a pore diameter of 40 micron and the oversized agglomerated particles therein were removed.

5) The suspension was centrifuged at 1200 rpm for 2 minutes, and the supernatant was removed.

6) 0.5 milliliter of sterile deionized water was added to 1 g of calcium hydrophosphate microparticles to prepare a paste by repeatedly vortex oscillation and stirring.

7) The calcium hydrophosphate microparticles were added into the decellularized microfiber matrix in a mass ratio of decellularized microfiber matrix to calcium hydrophosphate microparticle of 4:6.

8) The calcium hydrophosphate microparticles and the decellularized microfiber matrix were placed on a vortex mixer and fully mixed for one hour so that they were mixed homogeneously;

9) The mixture was centrifuged at 1200 rpm for 2 minutes, and the supernatant was removed.

10) 2 parts by weight of sterile physiological saline was added into 4 parts by weight of the decellularized matrix microfiber and 6 parts by weight of the calcium hydrophosphate microparticle.

Figure 2:
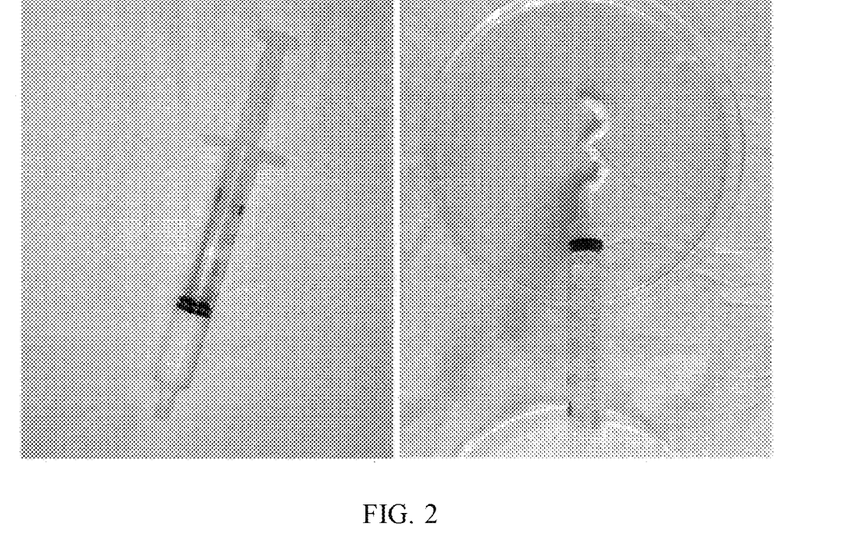
FIG. 2 shows the injectability of the biological tissue matrix/calcium hydrophosphate composite material.
Figure 3A:
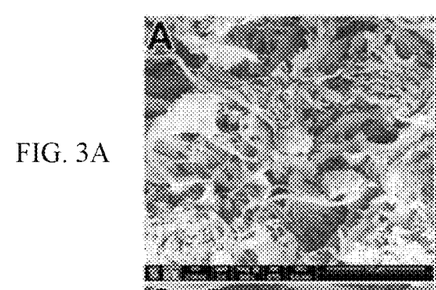
FIG. 3A is a scanning electron microscope image of the biological tissue matrix/calcium hydrophosphate composite material, showing typical morphology of the composite material.
Figure 3B:
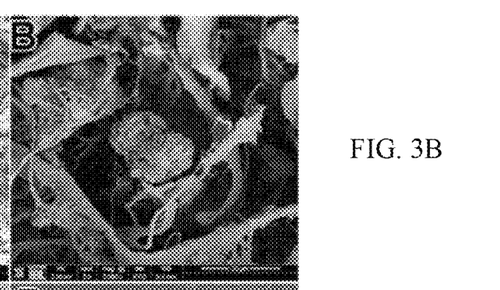
FIG. 3B is a scanning electron microscope image of the biological tissue matrix/calcium hydrophosphate composite material, showing distribution of the calcium hydrophosphate microparticles.
Figure 3C:
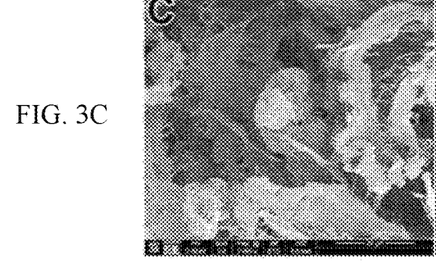
FIG. 3C is a scanning electron microscope image of the biological tissue matrix/calcium hydrophosphate composite material, showing distribution of the calcium hydrophosphate microparticles.
Figure 3D:
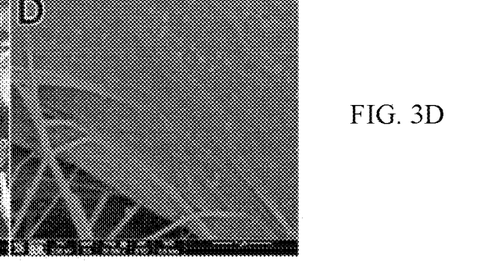
FIG. 3D is a scanning electron microscope image of the biological tissue matrix/calcium hydrophosphate composite material, showing triple-helix structure of collagen microfibers.

11) An injectable composite material was obtained after sufficient agitation. As shown in FIG. 2, this material can be applied to the patient's wound with a standard syringe;

12) The composite material was stored as paste, and the microstructure thereof was shown in FIGS. 3A-D. The scanning electron microscope image shows that the calcium hydrophosphate microparticles are evenly distributed around the decellularized matrix microfibers without obvious agglomeration. In addition, the image under high magnification shows that the decellularized matrix consists of a large amount of collagen fibers, and the collagen fiber completely maintains its natural triple helix structure and is distributed within the composite material as micelle.

Figure 4A:
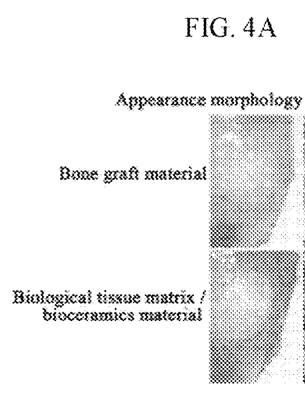
FIG. 4A shows an implantation experiment of calvarial defect repair using the biological tissue matrix/calcium hydrophosphate composite material, showing a gross view of the mouse calvarial defect after repair.
Figure 4B:
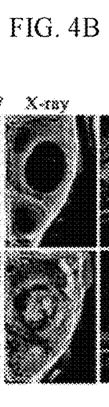
FIG. 4B shows an implantation experiment of calvarial defect repair using the biological tissue matrix/calcium hydrophosphate composite material, showing x-ray observations of the mouse calvarial defect after repair.
Figure 4C:
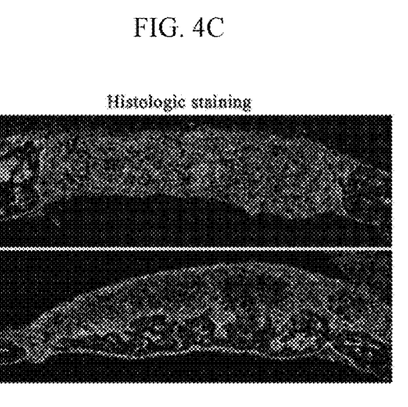
FIG. 4C shows an implantation experiment of calvarial defect repair using the biological tissue matrix/calcium hydrophosphate composite material, showing histological staining of the mouse calvarial defect after repair.

Example 2: Bone Defect Repair Experiment of the Injectable Biological Tissue Matrix/Calcium Hydrophosphate Composite Material The injectable biological tissue matrix/calcium hydrophosphate composite material prepared according to the present application was used to evaluate the bone forming ability of this material with a mouse calvarial defect model of nude mouse without thymus. The mice (6 cases) were anesthetized and then the head furs thereof were shaved off A 1 centimeter skin incision was cut along the sagittal suture of the mouse head. Circular defect with a diameter of 3.5 millimeter was made on the skull with a dental drill after putting the skin apart. The bone defect was filled with the material prepared according to the present invention, and then the wound was sutured. Six weeks later, the mice were sacrificed humanely. The skull after repairing was observed grossly. It is found that the material and the surrounding bone tissue integrated well. X-ray observation shows that a large amount of bones are formed at the defects. Histological observation also showed that new bone has successfully formed within the defect. It is found that the bone defects are filled with cells. The bone calcium staining shows that a large amount of bone calcium is deposited at the defects. The bone defects are completely bridged, as shown in FIGS. 4A-C. This example is the first which achieves repair of large area bone defect only by biological material, without adding any biological activity factor or stem cells.

Figure 5A:
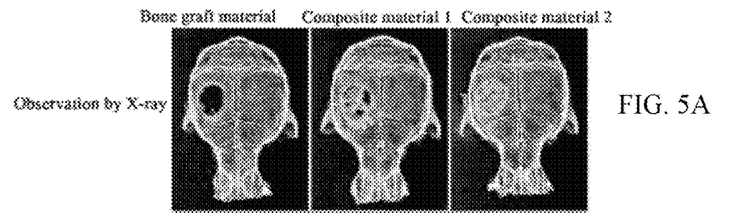
FIG. 5A shows an implantation experiment for repairing the mouse calvarial defect after combining the biological tissue matrix/calcium hydrophosphate composite material with fresh bone marrow, showing x-ray observations of the skull of the mouse after repair.
Figure 5B:
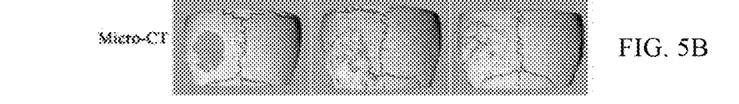
FIG. 5B shows an implantation experiment for repairing the mouse calvarial defect after combining the biological tissue matrix/calcium hydrophosphate composite material with fresh bone marrow, showing micro-CT Scanning of the skull of the mouse after repair.
Figure 5C:
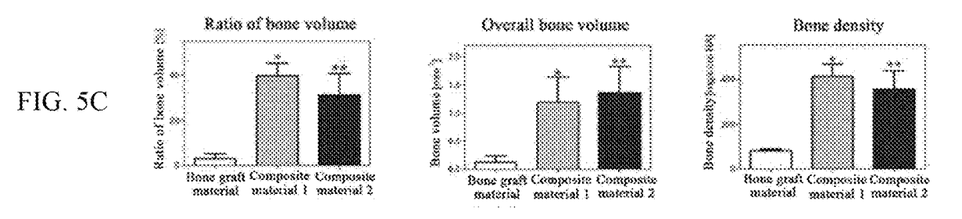
FIG. 5C shows an implantation experiment for repairing the mouse calvarial defect after combining the biological tissue matrix/calcium hydrophosphate composite material with fresh bone marrow, showing quantitative analysis of the micro-CT Scanning.
Figure 6A:
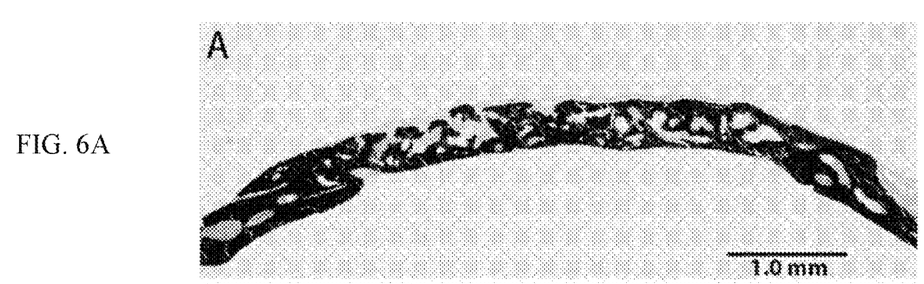
FIG. 6A shows the histological observation after repairing the skull of the mouse after combining the biological tissue matrix/calcium hydrophosphate composite material with fresh bone marrow using Von-Kassa staining (bone calcium deposition)
Figure 6B:
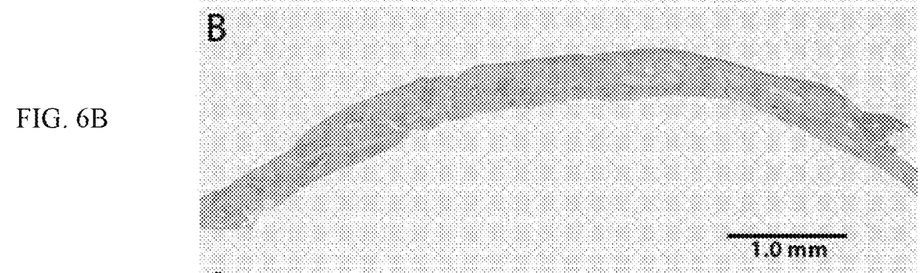
FIG. 6B shows the histological observation after repairing the skull of the mouse after combining the biological tissue matrix/calcium hydrophosphate composite material with fresh bone marrow using the MASSON trichrome staining method.
Figure 6C:
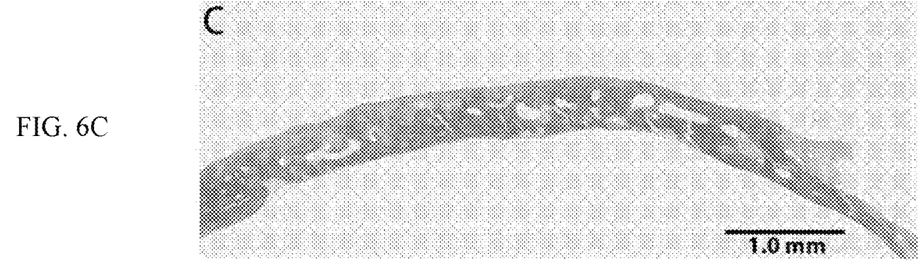
FIG. 6C shows the histological observation after repairing the skull of the mouse after combining the biological tissue matrix/calcium hydrophosphate composite material with fresh bone marrow using the hematoxylin-eosin staining method.

Example 3: Bone Defect Repair Experiment of the Injectable Biological Tissue Matrix/Calcium Hydrophosphate Composite Material as a Carrier for Fresh Bone Marrow The injectable biological tissue matrix/calcium hydrophosphate composite material prepared in Example 1 was mixed with fresh mouse bone marrow aspirate to prepare a paste-like material. The mouse model used in Example 2 was used. The bone defects were filled with the composite material loaded with fresh bone marrow aspirate, and then the wounds were sutured. Six weeks later, X-ray observations revealed that the entire bone defect was filled with newly formed bone tissue. No tissue gap was found at the edge of the bone defects. Micro-CT scanning showed the same results that the entire bone defect had been filled with newly formed bone tissues, and a seamless connection was formed between the new bone and the implant. Quantitative analysis of bone formation showed that the material prepared in Example 1 could form much more bones than Healos® (J&J product), and the bone density thereof was closer to the autologous bone tissue (FIGS. 5A-C). Histological observations showed that the entire bone defect had been bridged by mineralized bone tissue. A large amount of bone trabeculas had been formed. Masson trichrome staining indicated that a large amount of collagens were deposited at the bone defect site and osteoblasts were found in the new bone, demonstrating that they participated in the formation of new bones. The result of the hematoxylin-eosin staining method was consistent with the results obtained in the previous two staining methods. No fibrous tissue is found around the bone defects, and bone union was achieved, such that the repair method described in this example is a viable clinical strategy.

The foregoing is only an illustration of several specific embodiments of the present invention, but is not to be construed as limiting the scope of protection of the present invention. Equivalent changes or modifications in accordance the spirit of the invention are considered to fall within the protection scope of the present invention.

What claimed is:

1. An injectable composite material for bone repair, comprising the following raw materials in parts by weight: 1-7 parts of biological tissue matrix material, 1-9 parts of bioceramics, or minerals containing strontium, zinc, magnesium or silicon, or salts containing strontium, zinc, magnesium or silicon as a material for reinforcing phase, and 2-8 parts of physiological saline or other isotonic aqueous solution, wherein said biological tissue matrix material is an extracellular matrix maintaining its natural cross-linked structure, which is prepared from soft tissue of mammals, and consists essentially of collagen fibers, and wherein said biological tissue matrix material has a microfibrillar shape; the biological tissue matrix material with the microfibrillar shape has a diameter of 1 to 1500 micrometers; and the aspect ratio of the biological tissue matrix material with the microfibrillar shape is in the range of 0.05-0.95, and wherein said bioceramics or minerals containing strontium, zinc, magnesium or silicon, or salts containing strontium, zinc, magnesium or silicon are distributed in a form of microparticles within said biological tissue matrix material; and bioceramic, or minerals containing strontium, zinc, magnesium or silicon, or salts containing strontium, zinc, magnesium or silicon microparticles form a three-dimensional network structure in the biological tissue matrix material, wherein the bioceramic particles have a particle size of 1 to 500 micrometers, and wherein the biological tissue matrix material is obtained by micronizing tissue.

2. The injectable composite material for bone repair according to claim 1, wherein said soft tissue of mammals is a soft tissue from a pig, a soft tissue from a bovine, or a soft tissue from human body; said soft tissue is selected from the group consisting of skin, dermis, blood vessel, diaphragm, muscle tendon, ligament, large intestine, small intestine, and nerve tissue.

3. The injectable composite material for bone repair according to claim 1, wherein said bioceramics are hydroxyapatite, α-tricalcium phosphate, β-tricalcium phosphate, calcium hydrophosphate, calcium hydrophosphate dihydrate, calcium dihydrophosphate, tetracalcium phosphate, octacalcium phosphate, calcium sulfate, or calcium carbonate.

4. A method for preparing the injectable composite material for bone repair according to claim 1, comprising the following steps:
　　1) preparing a microfibrillar biological tissue matrix material, comprising the following steps:
　　　　1.1) collecting raw tissue material, cleaning blood off of the raw tissue material, cutting the raw tissue into strips having dimensions of 0.5-2 centimeters in width and 4-8 centimeters in length, and preserving the strips at −20° C.;
　　　　1.2) disinfecting and sterilizing the raw tissue material by:
　　　　　　sterilizing the raw tissue material by using ammonia aqueous solution with a weight percentage of 0.1%;

soaking the raw tissue material in the solution and slowly shaking for 6-36 hours;

washing the raw tissue material with sterile deionized water; and rinsing the raw tissue material with sterile physiological saline to produce a disinfected raw tissue material;

1.3) micronizing the disinfected raw tissue by homogenizing the disinfected raw tissue material with a grinder;

1.4) decellularizing the tissue with a decellularization solution, followed by removing remaining deoxyribonucleic acid with deoxyribonuclease solution, and removing α-galactoside with a solution for α-galactoside removal; inactivating one or more viruses with a mixture solution of hydrogen peroxide, acetic acid and peroxyacetic acid;

1.5) using physiological saline with a weight percent of 0.9% to wash the material resulting from step 1.4) three or more times to remove any residues resulting from step 1.4);

1.6) washing the material resulting from step 1.5) three or more times with sterile deionized water;

1.7) terminally sterilizing the material resulting from step 1.6) by Co60 gamma rays, X-rays or electron beams to form biological tissue matrix microfibers, sealing and storing the biological tissue matrix microfibers in a closed container, and preserving the biological tissue matrix microfibers in a buffer with neutral pH, said buffer comprising physiological saline and a phosphate buffer;

2) preparing bioceramic microparticles, comprising the following steps:

2.1) obtaining bioceramic microparticles with a particle size of 0.1-500 microns from a bioceramic by a process comprising mechanical pulverization, high-rate ball-milling, and sieving, and then disinfecting and sterilizing the bioceramic microparticles to inactivate one or more viruses located theron;

2.2) mixing the bioceramic microparticles with sterile physiological saline in a ratio of 1:1 to 1:5, and stirring and vibrating the mixture of bioceramic particles and sterile physiological saline to obtain a homogeneous suspension;

3) suspending the biological tissue matrix microfibers obtained in step 1.7) in an amount of physiological saline having a weight 1-5 times that of the microfibers, and shaking the suspension until the suspension is homogeneous;

4) mixing 1-9 parts of the bioceramic particles obtained from step 2.2) with 1-7 parts of the biological tissue matrix microfibers obtained from step3);

5) vortex mixing the resulting mixture in a container for one hour until the bioceramic particles are completely adsorbed onto the biological tissue matrix microfibers;

6) removing excess water from the vortexed mixture by centrifugation at 200 to 10000 rpm, and allowing the biological tissue matrix microfibers with bioceramic particles adsorbed thereon to be deposited on the bottom of the container in solid state;

7) adding an amount of physiological saline, blood, bone marrow, or platelet plasma having a weight 1-5 times that of the biological tissue matrix microfibers with bioceramic particles adsorbed thereon to form a fluid mixture, and vortex mixing the fluid mixture to form a homogeneous fluid mixture, wherein the moisture content of the homogeneous fluid mixture in mass percent is 20-80%;

8) sealing and storing the homogeneous fluid mixture in a closed container, and sterilizing the homogeneous fluid mixture with gamma rays, X-rays or electron beams.

5. The method for preparing the injectable composite material for bone repair according to claim 4, wherein said decellularization solution in step 1.4) contains 1 to 10% of sodium deoxycholate, 2 to 15 mM of ethylenediaminetetraacetic acid, and 10 to 50 mM of 4-hydroxyethyl piperazine ethanesulfonic acid per liter; the pH of said decellularization solution is 6.8 to 7.2; said deoxyribonuclease solution contains 10 to 50 mM of 4-hydroxyethyl piperazine ethanesulfonic acid, 1 to 20 mM of calcium chloride, and 1 to 20 mM of magnesium chloride and 0.5 to 5 mg of deoxyribonuclease per liter; said solution for α-galactoside removal contains 0.2 to 10 mg of α-galactosidase, and 2 to 40 mM of 4-hydroxyethyl piperazine ethanesulfonic acid per liter; the pH of said solution for α-galactoside removal is 5.0 to 7.5; and the solution used for inactivating one or more viruses is a mixture solution of 0.10% of hydrogen peroxide, 0.50% of acetic acid, and 0.50% of peroxyacetic acid.

6. The method for preparing the injectable composite material for bone repair according to claim 4, wherein the fluid mixture of step 7) is formed with blood, bone marrow, or platelet plasma.

7. The method for preparing the injectable composite material for bone repair according to claim 4, wherein the fluid mixture of step 7) is formed with physiological saline.

8. A method for delivering stem cells to a bone defect, comprising:

forming a cell suspension from bone marrow mesenchymal stem cells, adipose-derived stem cells or stem cells extracted from blood;

mixing the cell suspension with the injectable composite material for bone repair according to claim 1 to form a mixture; and delivering the mixture to the bone defect.

* * * * *